(12) United States Patent
Schwab et al.

(10) Patent No.: US 11,642,157 B2
(45) Date of Patent: May 9, 2023

(54) SURGICAL ROD BENDER

(71) Applicant: K2M, Inc., Leesburg, VA (US)

(72) Inventors: Frank Schwab, New York, NY (US);
Theo Choi, Arlington, VA (US);
Timmon Ark, Vienna, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 17/370,520

(22) Filed: Jul. 8, 2021

(65) Prior Publication Data

US 2021/0330366 A1 Oct. 28, 2021

Related U.S. Application Data

(62) Division of application No. 15/485,455, filed on Apr. 12, 2017, now Pat. No. 11,090,096.

(60) Provisional application No. 62/321,396, filed on Apr. 12, 2016.

(51) Int. Cl.
*B21F 1/00* (2006.01)
*B21F 45/00* (2006.01)
*A61B 17/88* (2006.01)
*A61B 17/70* (2006.01)

(52) U.S. Cl.
CPC ...... *A61B 17/8863* (2013.01); *A61B 17/7001* (2013.01); *B21F 1/002* (2013.01); *B21F 45/008* (2013.01)

(58) Field of Classification Search
CPC ... B21D 7/00; B21D 7/02; B21D 7/04; B21D 7/025; B21D 7/06; B21D 7/063; B21D 9/00; B21D 9/08; B21D 11/02; B21D 11/18; B21D 37/12
See application file for complete search history.

(56) References Cited

U.S. PATENT DOCUMENTS

| | | | |
|---|---|---|---|
| 1,369,676 A | 2/1921 | Kusisto | |
| 2,291,413 A * | 7/1942 | Siebrandt | A61B 17/8861 606/103 |
| 2,455,609 A | 12/1948 | Scheib | |
| 5,649,572 A | 7/1997 | Lile | |
| 7,823,856 B2 | 11/2010 | Schwartz et al. | |
| 8,327,682 B2 | 12/2012 | Haase et al. | |
| 8,506,603 B2 | 8/2013 | McClintock et al. | |
| 9,295,494 B2 | 3/2016 | Strauss et al. | |
| 9,820,793 B1 * | 11/2017 | Wade | A61B 17/8869 |

* cited by examiner

*Primary Examiner* — Teresa M Ekiert
(74) *Attorney, Agent, or Firm* — Lerner David LLP

(57) ABSTRACT

An instrument for bending a surgical rod includes first and second arm assemblies. The first arm assembly includes first and second arms having respective first and second receiving portions configured to receive the surgical rod therein. The second arm assembly includes third and fourth arms having respective third and fourth receiving portions configured to receive the surgical rod therein. The instrument is reconfigurable from an initial configuration in which the first and third receiving portions of the respective first and third arms engage the surgical rod such that spreading of the first and third receiving portions in a first direction bends the surgical rod in a first orientation and spreading of the first and third receiving portions in a second direction bends the surgical rod in a second orientation opposite to the first orientation.

20 Claims, 5 Drawing Sheets

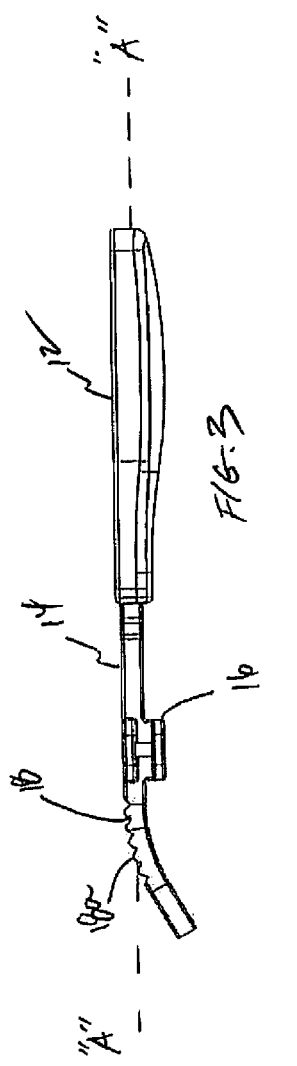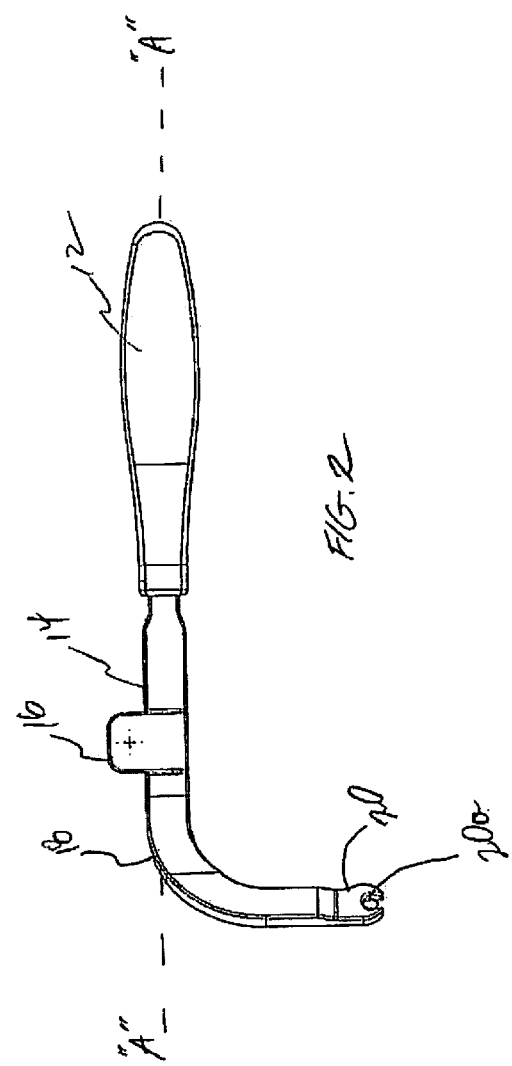

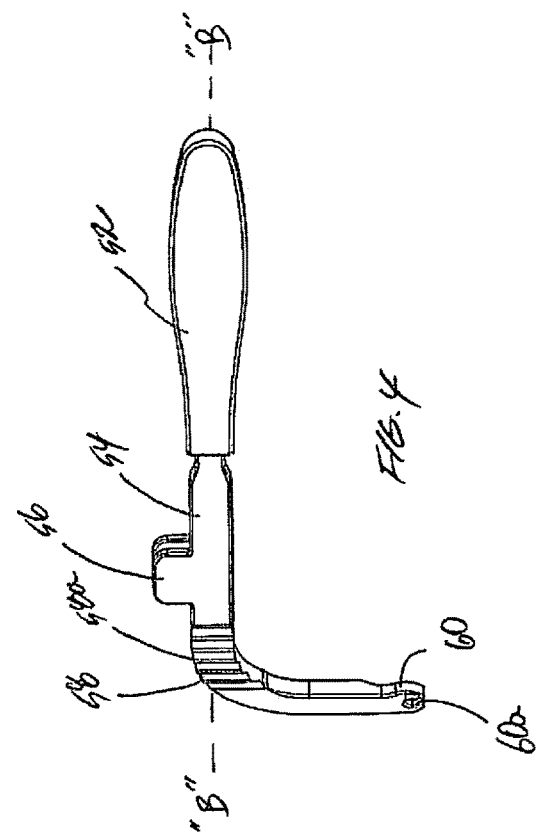
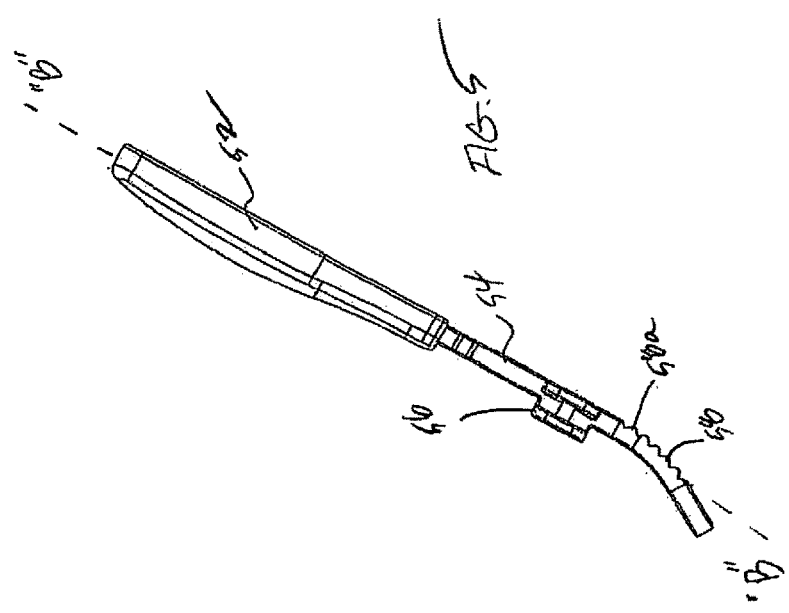

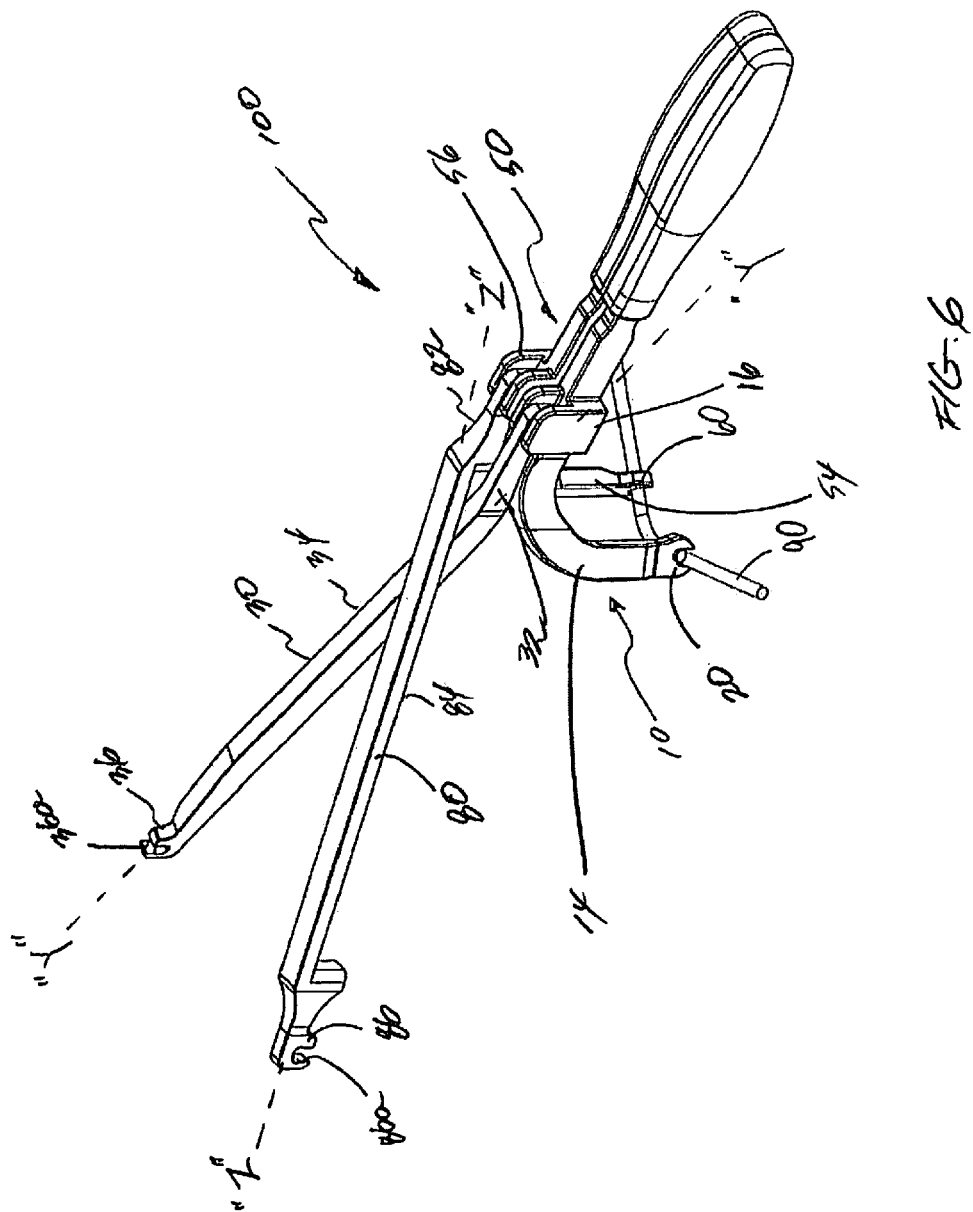

SURGICAL ROD BENDER

CROSS-REFERENCE TO RELATED APPLICATIONS

The present application is a divisional of U.S. patent application Ser. No. 15/485,455, filed on Apr. 12, 2017, which claims the benefit of the filing date of U.S. Provisional Patent Application No. 62/321,396, filed on Apr. 12, 2016, the disclosures of which are hereby incorporated herein by reference.

BACKGROUND

Technical Field

The present disclosure relates to a surgical instrument, and more particularly, to a surgical rod bender.

Background of Related Art

The spine is a flexible structure capable of a large range of motion. There are various disorders, diseases, and types of injury, which restrict the range of motion of the spine or interfere with important elements of the nervous system. The problems include scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages, and cadaver and human bone implants. In order to facilitate stabilizing the spine and keeping the interbody in position, other implants are commonly employed, such as spinal rods. Spinal rods are typically made of cobalt chrome, stainless steel, or titanium alloy. However, in order to transition to a less stiff construct at the top, other less rigid materials and rod shapes may be employed to provide the desired stiffness.

Therefore, there is a continuing need for a device that can create varying severities or contours of bend in a surgical rod to meet the needs of each patient, while expediting the surgical process.

SUMMARY

In accordance with an embodiment of the present disclosure, there is provided an instrument for bending a surgical rod. The instrument includes first and second arm assemblies. The first arm assembly includes first and second arms. The first and second arms include respective first and second receiving portions configured to receive the surgical rod therein. The second arm assembly includes third and fourth arms. The third and fourth arms include respective third and fourth receiving portions configured to receive the surgical rod therein. The instrument is reconfigurable from an initial configuration in which the first and third receiving portions of the respective first and third arms engage the surgical rod such that spreading of the first and third receiving portions in a first direction bends the surgical rod in a first orientation and spreading of the first and third receiving portions in a second direction bends the surgical rod in a second orientation opposite to the first orientation.

In an embodiment, the first and third receiving portions of the respective first and third arms of the first and second arm assemblies may each define a notch configured to receive the surgical rod therein.

In another embodiment, the surgical rod in the first orientation may define a convex profile. In addition, the surgical rod in the second orientation may define a concave profile.

In an embodiment, the first and third receiving portions in the initial configuration may be in a planar contact.

In an embodiment, the first and third arms of the first and second arm assemblies may each include an L-shaped profile.

In another embodiment, the second and fourth arms of the first and second arm assemblies may be hingedly connected to the respective first and third arms of the first and second arm assemblies.

In an embodiment, the first arm of the first arm assembly may further include a handle, and the first receiving portion of the first arm may be offset from a longitudinal axis defined by the handle. In addition, the first and third arms of the respective first and second arm assemblies may include a mating structure to provide incremental spreading of the handles. In particular, the mating structure may include a plurality of teeth.

In accordance with another embodiment of the present disclosure, there is provided an instrument for bending a surgical rod. The instrument includes first and second arm assemblies. The first arm assembly includes first receiving portion configured to receive the surgical rod therein. The second arm assembly includes second receiving portion configured to receive the surgical rod therein. The first and second arm assemblies are detachably associated with each other. The instrument is selectively configurable from an initial configuration to a first configuration in which the first and second receiving portions engage the surgical rod for bending the surgical rod in a first orientation and from the initial configuration to a second configuration in which the first and second receiving portions engage the surgical rod for bending the surgical rod in a second orientation opposite to the first orientation.

BRIEF DESCRIPTION OF THE DRAWINGS

The above and other aspects and features of the present disclosure will become more apparent in light of the following detailed description when taken in conjunction with the accompanying drawings in which:

FIG. 2 is a side view of a first arm of a first arm assembly of the rod bending device of FIG. 1;

FIG. 3 is a top view of the first arm of the first arm assembly of FIG. 2;

FIG. 4 is a side view of a first arm of a second arm assembly of the rod bending device of FIG. 1;

FIG. 5 is a top view of the first arm of the second arm assembly of FIG. 4;

FIG. 6 is a perspective view of the rod bending device of FIG. 1 illustrating use in a first configuration.

DETAILED DESCRIPTION

Figure 1:
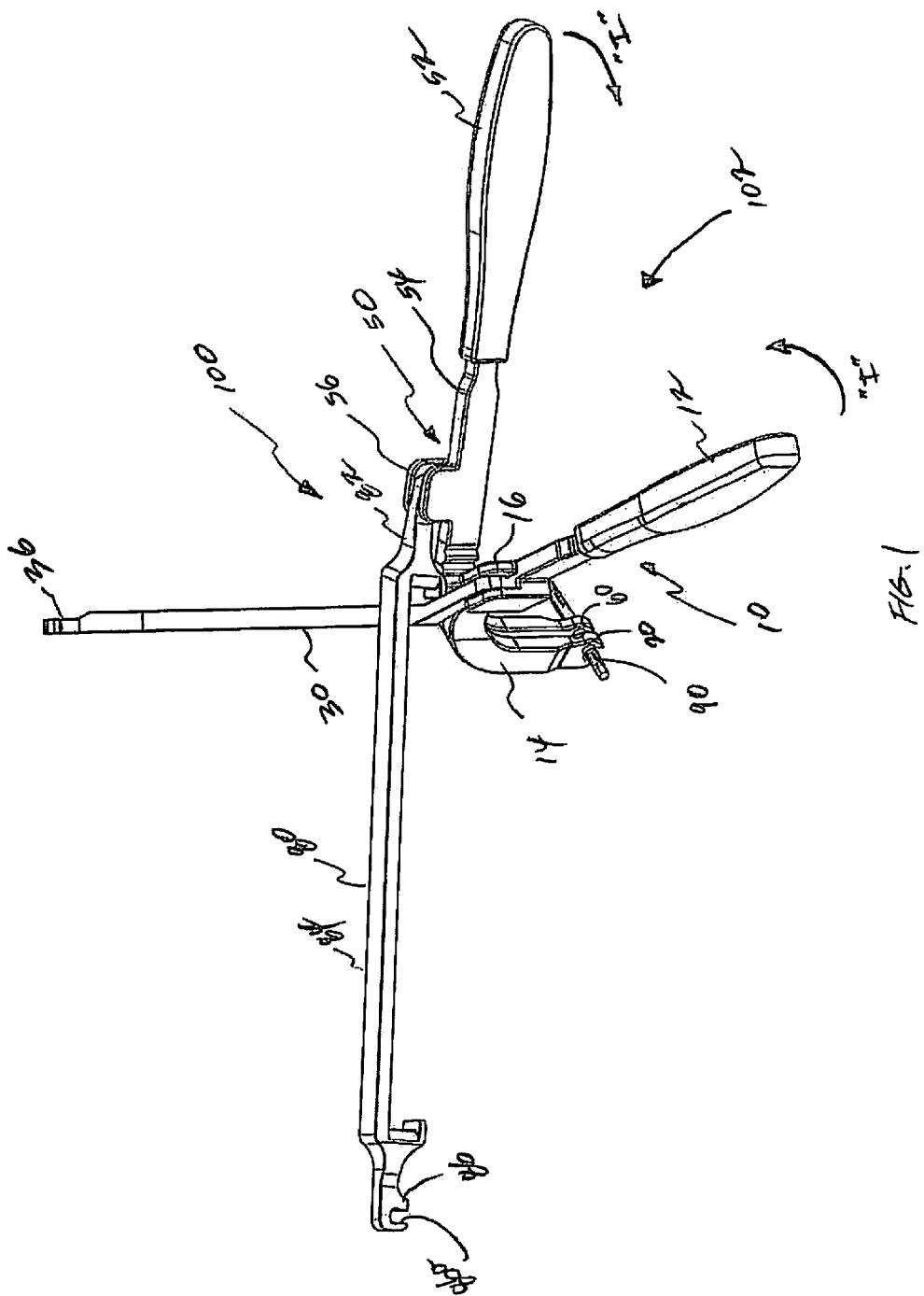
FIG. 1 is a perspective view of a rod bending device in accordance with an embodiment of the present disclosure illustrating an initial configuration of the rod bending device.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction toward a patient's head, whereas the term "caudad" indicates a direction toward the patient's feet. Further still, the term "medial" indicates a direction toward the middle of the body of the patient, while the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

With reference to FIG. 1, an embodiment of the present disclosure is shown generally as a rod bender 100 selectively configurable to create varying severities or contours of bend in a surgical rod 90. For example, rod bender 100 in a first configuration (FIG. 6) may create a convex bend in surgical rod 90, and rod bender 100 in a second configuration (FIG. 7) may create a concave bend in surgical rod 90, as will be described hereinbelow. Rod bender 100 may be utilized prior to fixating spinal rod 90 in a patient, i.e., surgical rod 90 may be bent prior to being inserted in the patient, or in-situ. Rod bender 100 may be made of titanium, titanium alloy, stainless steel, cobalt chrome, a combination thereof, or any other suitable biocompatible material. Surgical rod 90 is utilized to secure vertebral bodies and/or an intervertebral cage interposed between adjacent vertebral bodies to promote spinal fusion. Reference may be made to U.S. Pat. No. 9,295,494 filed on Nov. 8, 2012, entitled "Spinal Stabilization System," the entire content of which is incorporated herein by reference, for a detailed discussion of the construction and operation of a surgical rod.

With reference to FIG. 1, rod bender 100 includes first and second arm assemblies 10, 50. First and second arm assemblies 10, 50 are selectively mated to achieve varying severities or contours of bend such as, e.g., a convex bend (FIG. 6) or a concave bend (FIG. 7), in surgical rod 90. First and second arm assemblies 10, 50 are detachable and may be operatively mated through engagement with surgical rod 90.

With reference now to FIGS. 1-3, first arm assembly 10 includes a handle 12, a first arm 14 extending from handle 12, and a second arm 30 coupled with first arm 14. First arm 14 includes a hinge portion 16. Second arm 30 is hingedly connected with first arm 14 at hinge potion 16. First arm 14 may define a substantially L-shaped profile. First arm 14 further includes an engaging portion 18 having teeth 18a configured to engage a corresponding structure on a first arm 54 of second arm assembly 50 to enable stable and incremental bending of surgical rod 90. In addition, first arm 14 further includes a first receiving portion 20 defining a U-shaped notch 20a configured to receive surgical rod 90 therein. Handle 12 defines a longitudinal axis "A-A," and at least a portion of engaging portion 18 and receiving portion 20 extend transversely outward, thereby defining an acute angle with respect to longitudinal axis "A-A." Under such a configuration, when first and third receiving portions 20, 60 of first and second arm assemblies 10, 50 engage surgical rod 90 in the initial configuration, handles 12, 52 of first and second arm assemblies 10, 50 define a gap 102 therebetween.

With particular reference to FIGS. 1 and 6, second arm 30 of first arm assembly 10 includes a connecting portion 32 hingedly connected to hinge portion 16 of first arm 14. In particular, second arm 30 is detachably coupled to hinge portion 16 of first arm 14. Second arm 30 further includes an elongate body 34 extending between connecting portion 32 and a second receiving portion 36 defining a U-shaped notch 36a dimensioned to receive surgical rod 90 therein. Elongate body 34 and second receiving portion 36 define a longitudinal axis "Y-Y." Connecting portion 32 is slightly bent transversely outward, thereby defining an acute angle with respect to longitudinal axis "Y-Y". In addition, U-shaped notch 36a may be defined transverse to longitudinal axis "Y-Y."

With reference now to FIGS. 1, 4, and 5, second arm assembly 50 is substantially identical to first arm assembly 10. Identical constructions will not be described in detail to avoid obscuring the present disclosure in unnecessary detail. Second arm assembly 50 includes a handle 52, a first arm 54 extending from handle 52, and a second arm 80 detachably coupled with first arm 54. First arm 54 includes a hinge portion 56. Second arm 80 is hingedly connected with first arm 54 at hinge potion 56. First arm 54 further includes an engaging portion 58 having teeth 58a configured to engage engaging portion 18 of first arm 14 of first arm assembly 10 to enable stable and incremental bending of surgical rod 90. In addition, first arm 54 further includes a third receiving portion 60 defining a U-shaped notch 60a configured to receive surgical rod 90 therein. Handle 52 defines a longitudinal axis "B-B," and at least a portion of engaging portion 58 and third receiving portion 60 extend transversely outward, thereby defining an acute angle with respect to longitudinal axis "B-B". First and third receiving portions 20, 60 of first and second arm assemblies 10, 50 engage surgical rod 90 in the initial configuration and are transitioned to the first or second configuration to create a desirable bend in surgical rod 90. Handles 12, 52 of respective first and second arm assemblies 10, 50 define gap 102 therebetween in the initial configuration to facilitate relative movement of handles 12, 52.

With particular reference to FIGS. 1 and 6, second arm 80 of second arm assembly 50 includes a connecting portion 82 hingedly connected to hinge portion 56 of first arm 54. Second arm 80 further includes an elongate body 84 extending between connecting portion 82 and a fourth receiving portion 86 defining a U-shaped notch 86a dimensioned to receive surgical rod 90 therein. Elongate body 84 and fourth receiving portion 86 define a longitudinal axis "Z-Z." Connecting portion 82 defines an acute angle with respect to longitudinal axis "Z-Z." In addition, U-shaped notches 36a, 86a may be transversely defined with respect to respective longitudinal axes "Y-Y," "Z-Z", in opposite directions to further secure surgical rod 90 received therein.

Figure 7:
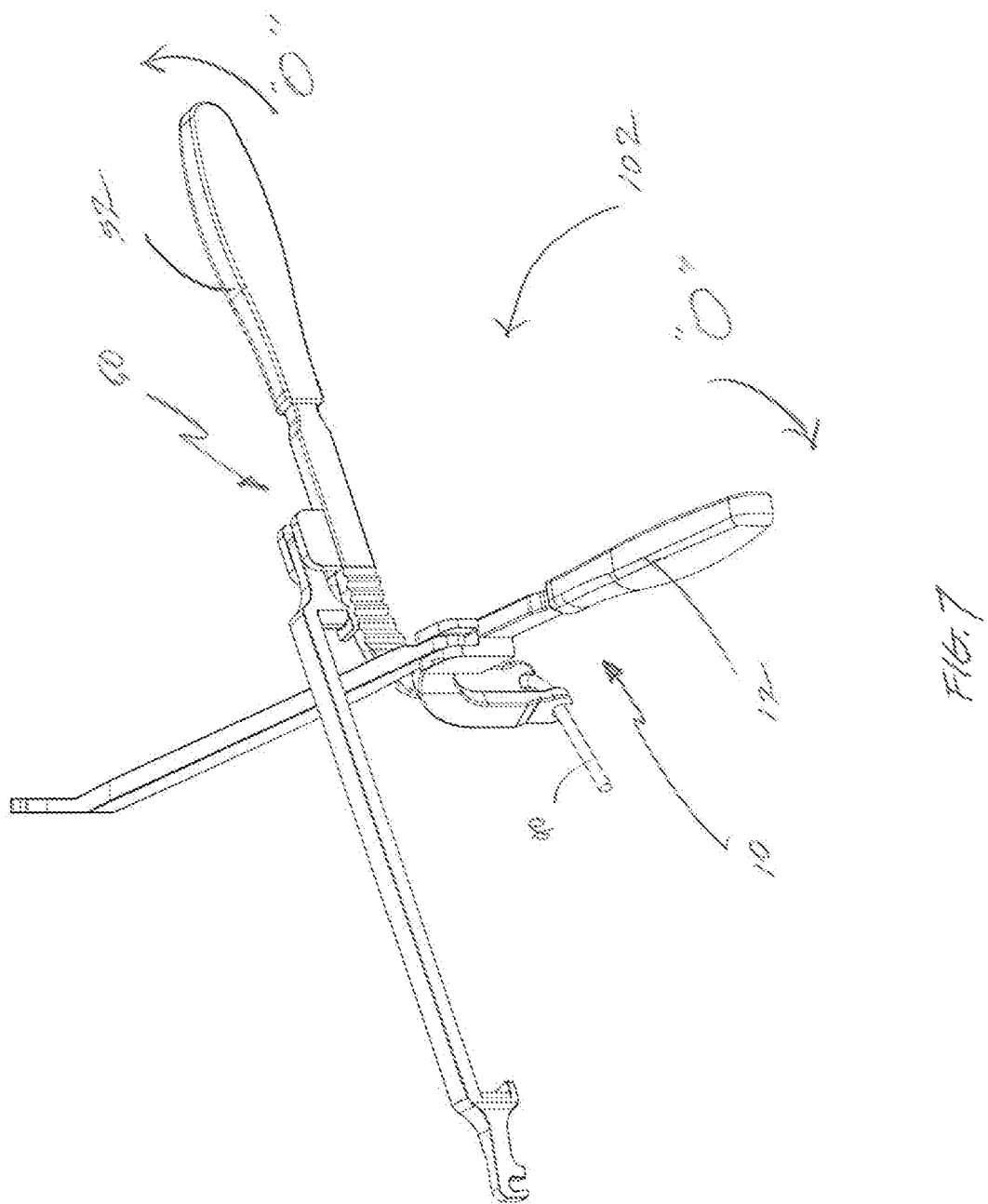
FIG. 7 is a perspective view of the rod bending device of FIG. 1 illustrating use in a second configuration.

In use, first and second arm assemblies 10, 50 may be selectively mated for a desired contour of surgical rod 90. For example, rod bender 100 may be placed in the initial configuration in which first and third receiving portions 20, 60 of respective first arms 14, 54 of first and second arm assemblies 10, 50 engage surgical rod 90 to create convex (FIG. 6) or concave (FIG. 7) bends in surgical rod 90. Initially, surgical rod 90 is positioned within U-shaped notches 20a, 60a of respective first and third receiving portions 20, 60 of first and second arm assemblies 10, 50. This can be done prior to surgical rod 90 being placed within the patient or in-situ. At this time, first and third receiving portions 20, 60 may be, e.g., in planar contact with or substantially parallel to, each other. Such placement of first and third receiving portions 20, 60 provides gap 102 between handles 12, 52, which facilitates manipulation of handles 12, 52. At this time, handles 12, 52 may be approximated toward each other in an inward direction as shown by arrows "I" (FIG. 1) to effect convex bending of surgical rod 90 (FIG. 6). Alternatively, handles 12, 52 may be approximated away from each other in an outward direction as shown by arrows "O" (FIG. 7) to effect concave bending of surgical rod 90 (FIG. 7). Under such a configuration, rod bender 100 may create a bend in surgical rod 90 that is, e.g., 90 degrees or more. It is contemplated that U-shaped notches 36a, 86a of second and fourth receiving portions 36, 86 of respective second arms 30, 80 of first and second arm assemblies 10, 50 may be utilized to created bends in surgical rod 90.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method of use, comprising:
   providing an instrument for bending a surgical rod including:
   a first arm assembly including a first handle and a first arm extending from the first handle, the first arm having a first receiving portion, a first bend and a first plurality of teeth along the first bend; and
   a second arm assembly including a second handle and a second arm extending from the second handle, the second arm having a second receiving portion, a second bend and a second plurality of teeth along the second bend, the first bend and second bend being detachably associated with each other;
   engaging the first receiving portion of the first arm and the second receiving portion of the second arm with the surgical rod; and
   bending the surgical rod through the engagement of the first plurality of teeth with the second plurality of teeth such that approximating the first and second handles in a first direction bends the surgical rod in a first orientation and approximating the first and second handles in a second direction different from the first direction bends the surgical rod in a second orientation different to the first orientation.

2. The method according to claim 1, wherein bending the surgical rod includes approximating the first and second handles towards each other to create a convex profile in the surgical rod.

3. The method according to claim 1, wherein bending the surgical rod includes approximating the first and second handles away from each other to create a concave profile in the surgical rod.

4. The method according to claim 1, wherein engaging the first and second receiving portions of the respective first and second arms with the surgical rod includes placing the first and second receiving portions of the respective first and second arm assemblies in planar contact.

5. The method according to claim 1, wherein bending the surgical rod includes approximating the first handle in a third direction relative to the second handle and approximating the first receiving portion in a fourth direction relative to the second receiving portion, the first direction being opposite the second direction.

6. The method according to claim 1, further comprising engaging a third arm to the first arm assembly and a fourth arm to the second arm assembly, the third arm having a third receiving portion at a first end of the third arm and the fourth arm having a fourth receiving portion at a first end of the fourth arm.

7. The method according to claim 6, wherein the third arm is engaged to the first arm assembly and the fourth arm is engaged to the second arm assembly such that the third arm is at least partially received within the fourth arm.

8. The method according to claim 6, wherein bending the surgical rod includes rotating the third arm relative to the fourth arm.

9. The method according to claim 6, wherein engaging the third arm to the first arm assembly and the fourth arm to the second arm assembly includes engaging a connecting portion of the third arm to a hinge portion of the first arm assembly and a connecting portion of the fourth arm to a hinge portion of the second arm assembly, the connecting portions of the third arm and fourth arm being opposite the respective first ends.

10. The method according to claim 9, wherein engaging the connecting portion of the third arm to the hinge portion of the first arm assembly includes engaging the connecting portion of the third arm to lie substantially along a same direction as the first handle of the first arm, and engaging the connecting portion of the fourth arm to the hinge portion of the second arm assembly includes engaging the connecting portion of the fourth arm to lie substantially along a same direction as the second handle of the second arm.

11. A method of use, comprising:
    engaging a first receiving portion of a first arm of a first arm assembly of a surgical instrument with a surgical rod;
    engaging a second receiving portion of a second arm of a second arm assembly of the surgical instrument with the surgical rod;
    approximating the surgical instrument to bend the surgical rod by engaging a first plurality of teeth of a first bend of the first arm and a second plurality of teeth of a second bend of the second arm to bend the surgical rod such that approximating a first handle of the first arm and a second handle of the second arm in a first direction bends the surgical rod in a first orientation, and approximating the first handle and the second handle in a second direction different than the first direction bends the surgical rod in a second orientation different than the first orientation, the first bend and the second bend being detachably associated with each other.

12. The method according to claim 11, wherein approximating the surgical instrument includes approximating the first and second handles towards each other to create a convex profile in the surgical rod.

13. The method according to claim 11, wherein approximating the surgical instrument includes approximating the first and second handles away from each other to create a concave profile in the surgical rod.

14. The method according to claim 11, wherein engaging the first and second receiving portions of the respective first and second arms with the surgical rod includes placing the first and second receiving portions of the respective first and second arm assemblies in planar contact.

15. The method according to claim 11, wherein approximating the surgical rod includes approximating the first handle in a third direction relative to the second handle and approximating the first receiving portion in a fourth direction relative to the second receiving portion, the first direction being opposite the second direction.

16. The method according to claim 11, further comprising engaging a third receiving portion at a first end of a third arm to the first arm assembly and a fourth receiving portion at a first end of a fourth arm to the second arm assembly.

17. The method according to claim 16, wherein the third arm is engaged to the first arm assembly and the fourth arm is engaged to the second arm assembly such that the third arm is at least partially received within the fourth arm.

18. The method according to claim 16, wherein approximating the surgical instrument includes moving the third arm within the fourth arm.

19. The method according to claim 16, wherein engaging the third arm to the first arm assembly and the fourth arm to the second arm assembly includes engaging a connecting portion of the third arm to a hinge portion of the first arm assembly and a connecting portion of the fourth arm to a hinge portion of the second arm assembly, the connecting portions of the third arm and fourth arm being opposite the respective first ends.

20. A method comprising:
placing a first portion of a rod in a first receiving portion of a first arm assembly;
placing a second portion of the rod in a second receiving portion of a second arm assembly;
grasping a first handle of the first arm assembly;
grasping a second handle of the second arm assembly;
engaging a first plurality of teeth of a first bend of the first arm assembly with a second plurality of teeth of a second bend of the second arm assembly;
moving the first and second handles to bend the rod, wherein moving the handles in a first direction bends the surgical rod in a first orientation and moving the handles in a second direction different from the first direction bends the surgical rod in a second orientation different from the first orientation.

\* \* \* \* \*